US 6,682,926 B2

(12) United States Patent
Lehmann et al.

(10) Patent No.: US 6,682,926 B2
(45) Date of Patent: Jan. 27, 2004

(54) DEVICE FOR PACKAGING A CHIP SHAPED CARRIER AND PROCESS FOR ASSEMBLING A PLURALITY OF SUCH CARRIERS

(75) Inventors: Thomas Lehmann, Lucerne (CH); Peter Vischer, Küssnacht am Rigi (CH)

(73) Assignee: Roche Molecular Systems, Inc., Alameda, CA (US)

( * ) Notice: Subject to any disclaimer, the term of this patent is extended or adjusted under 35 U.S.C. 154(b) by 139 days.

(21) Appl. No.: 09/879,239

(22) Filed: Jun. 8, 2001

(65) Prior Publication Data

US 2002/0019044 A1 Feb. 14, 2002

(30) Foreign Application Priority Data

Jun. 8, 2000 (EP) .............................. 00810501

(51) Int. Cl.[7] .................................. C12M 1/34
(52) U.S. Cl. ............................. 435/287.2; 435/288.3; 435/288.7; 435/809; 422/104; 356/246; 359/398
(58) Field of Search .................. 435/283.1, 287.2, 435/288.3, 293.1, 305.1, 305.4, 809, 6, 288.7; 422/99, 102, 104; 359/398; 356/246

(56) References Cited

U.S. PATENT DOCUMENTS

| 4,974,952 A | * | 12/1990 | Focht | 359/398 |
| 5,665,599 A | * | 9/1997 | Minuth | 435/288.3 |
| 5,945,334 A | * | 8/1999 | Besemer et al. | 435/287.2 |

FOREIGN PATENT DOCUMENTS

| EP | 201780 A1 | * | 11/1986 | G02B/21/34 |
| EP | 270363 A2 | * | 6/1988 | G01N/1/28 |
| EP | 547709 A2 | * | 6/1993 | B01L/3/00 |
| FR | 2784751 A1 | * | 4/2000 | C12Q/1/68 |
| FR | 2796571 A1 | * | 1/2001 | B01J/19/00 |
| JP | 09145583 A | * | 6/1997 | G01N/5/02 |
| WO | WO 200145843 A2 | * | 6/2001 | B01L/3/00 |

* cited by examiner

Primary Examiner—William H. Beisner
(74) Attorney, Agent, or Firm—Bart Wise; Charles Doyle (57) ABSTRACT

The invention provides devices for packaging a chip shaped carrier having an active surface which is adapted to be read by an electro-optical reading device, e.g. a surface which carries an array of DNA oligonucleotides. The invention further provides processes for assembling the devices. The invention also provides systems for carrying out evaluations and/or monitoring methods involving electro-optical reading of an activce surface of a chip shaped carrier.

32 Claims, 7 Drawing Sheets

DEVICE FOR PACKAGING A CHIP SHAPED CARRIER AND PROCESS FOR ASSEMBLING A PLURALITY OF SUCH CARRIERS

FIELD OF THE INVENTION

The present invention relates to a device for packaging a chip shaped carrier having an active surface which is adapted to be read by an electro-optical reading device.

The invention further relates to a process for assembling a plurality of such chip packaging devices.

The invention further relates to a system for carrying out evaluation and/or monitoring methods involving electro-optical reading of an active surface of a chip shaped carrier.

BACKGROUND OF THE INVENTION

Within the context of the instant invention a chip shaped carrier is a substrate, in particular a glass chip of e.g. squared shape having a thickness of e.g. 0.7 or 1.0 millimeter and a so called active surface, which is a surface coated with an array of different snippets of DNA, e.g. DNA oligonucleotide probes, located at known positions of that surface. Those snippets of DNA serve as probes for detecting DNA fragments with a complementary DNA sequence.

Within the context of the instant invention a packaging device for packaging such a DNA chip is in particular a one-way cartridge made of a plastic material.

DNA chips contained in such cartridges have a wide range of applications. For example, they may be used for understanding the structure-activity relationship between different biological materials or determining the DNA-sequence of an unknown biological material. For instance, the DNA-sequence of such unknown material may be determined by, for example, a process known as sequencing by hybridization. In one method of sequencing by hybridization, a sequences of diverse materials are formed at known locations on a surface of a chip, and a solution containing one or more targets to be sequenced is applied to that surface. The targets will bind or hybridize with only complementary sequences on the substrate. The locations at which hybridization occurs are detected with appropriate detection systems by labeling the targets with a fluorescent dye, radioactive isotope, enzyme, or other marker. Information about target sequences can be extracted from the data obtained by such detection systems.

By combining various available technologies, such as photolithography and fabrication techniques, substantial progress has been made in the fabrication and placement of diverse materials on chips of the above mentioned kind. For example, thousands of different sequences may be fabricated on a single substrate of about 1.28 square centimeter in only a small fraction of the time required by conventional methods. Such improvements make these substrates practical for use in various applications, such as biomedical research, clinical diagnostics, and other industrial markets, as well as the emerging field of genomics, which focuses on determining the relationship between genetic sequences and human physiology.

As commercialization of such chips becomes widespread, an economically feasible and device and a method for packaging the chips with a high-throughput are desired.

Since the active coating of the chip, that is the surface thereof of which is coated with the above mentioned diverse sequences, has to be accessible e.g. to optical detection means, e.g. in the case of fluorescence measurements, the chip has to be inserted into the outer wall of a one-way cartridge, and its active coating faces the interior of the so-called process chamber within the cartridge.

For instance in the above mentioned method of sequencing by hybridization, processing of the active coating of the chip includes flooding of the process chamber of the cartridge with a solution containing one or more targets to be sequenced. Therefore, a liquid-tight connection between the chip and the one-way cartridge is necessary. In a known embodiment described in Specification U.S. Pat. No. 5,945,334 this has been achieved under clean-room conditions by attaching the chip to a cavity of the cartridge by means of an adhesive, that is by gluing it into the cartridge. This known method for connecting the chip to the cartridge has two serious disadvantages. First, the fluorescence of the adhesives used is so high that it substantially interferes and perturbates fluorescence measurements performed on the active coating of the chips and can even have saturating effect on a photomultiplier used for performing the fluorescence measurements. A further disadvantage of the known method for connecting the chip to the cartridge is that it is performed manually and is not suitable for being performed by automated means.

SUMMARY OF THE INVENTION

A first aim of the invention is therefore to provide a device for packaging a chip of the above mentioned kind which does not have the above mentioned disadvantages and which provided a liquid-tight connection of such a chip to a cartridge, without using any adhesive substance, the structure of such a device being suitable for automated assembly thereof under clean-room conditions.

A second aim of the invention is to provide a process for assembling a plurality of chip packaging devices according to the invention with a high throughput.

A third aim of the invention is to provide a system for carrying out evaluation and/or monitoring methods involving electro-optical reading of an active surface of a chip shaped carrier without having the above mentioned disadvantages of prior art embodiments.

According to a first aspect of the invention the above mentioned first aim is attained with a device for packaging a chip shaped carrier having an active surface which is adapted to be read by an electro-optical reading device, said device comprising (a) a cartridge having an opening for introducing a liquid sample into said cartridge said cartridge comprising a casing part, (b) said casing part having an inner surface and outer surface, a first cavity for receiving a chip shaped carrier, and means which provide visual access to said first cavity, and thereby to said active surface of said chip shaped carrier, said first cavity having a bottom surface and inclined side wall surfaces which extend between said outer surface of said casing part and said bottom surface and which form an obtuse angle with that bottom surface, (c) a sealing frame which is part of said casing part and which is made of a compressible material, said sealing frame being connected to said bottom surface of said first cavity, and (d) a locking frame, (e) the shape and dimensions of said first cavity said chip shaped carrier, said sealing frame, and said locking frame, being such that (e.1) said chip shaped carrier fits into the space delimited by said sealing frame, and a gap exists between said sealing frame and the inclined side wall surfaces of said first cavity, (e.2) said locking frame, is larger than said gap, said locking frame is however insertable into said gap, by pressure exerted on said locking frame against said casing part, said pressure causing a compression of said sealing frame and a corresponding pressure on a substantial part of the outer surface of the lateral periphery of said chip shaped carrier, said outer surface being in contact with said sealing frame.

According to a second aspect of the invention the above mentioned first aim is attained with a device for packaging a chip shaped carrier having an active surface which is adapted to be read by an electro-optical reading device, said device comprising (a) a cartridge having an opening for introducing a liquid sample into said cartridge, said cartridge comprising a casing part, (b) said casing part having an inner surface and outer surface, a first cavity for receiving a chip shaped carrier, and means which provide visual access to said first cavity, and thereby to said active surface of said chip shaped carrier, said first cavity having a bottom surface and inclined side wall surfaces which extend between said inner surface of said casing part and said bottom surface and which form an obtuse angle with that bottom surface, (c) a sealing frame which is part of said casing part and which is made of a compressible material, said sealing frame being connected to said bottom surface of said first cavity, and (d) a locking frame, (e) the shape and dimensions of said first cavity, said chip shaped carrier, said sealing frame, and said locking frame being such that (e.1) said chip shaped carrier fits into the space delimited by said sealing frame and a gap exists between said sealing frame and the inclined side wall surfaces of said first cavity, (e.2) said locking frame is larger than said gap, said locking frame is however insertable into said gap by pressure exerted on said locking frame against said casing part, said pressure causing a compression of said sealing frame and a corresponding pressure on a substantial part of the outer surface of the lateral periphery of said chip shaped carrier, said outer surface being in contact with said sealing frame.

The main advantages of a chip packaging device according to the invention are due to the fact that the required liquid-tight connection of the chip to the cartridge is achieved without using any adhesive. These advantages are the absence of perturbating fluorescence related to the means used for making that connection and a longer useful lifetime of unused chips. In addition the coplanar arrangement of the chip and the means for establishing its liquid-tight connection to the cartridge provide improved flow conditions within the process chamber of the cartridge. Moreover, the structure of a chip packaging device according to the invention is suitable for a fully automated, high throughput assembly thereof.

According to the invention the above mentioned second aim is attained with a process for assembling a plurality of chip packaging devices according to the invention, said process comprising (a) providing a plurality of casing parts and a plurality of said locking frames to an automated assembly line, each of said casing parts comprising a sealing frame, (b) providing a plurality of chip shaped carriers having each an active surface to said assembly line, (c) positioning each of said chip shaped carriers within a sealing frame of one of said casing parts by means of a first automatic apparatus, (d) inserting each of said locking frames into a gap between said sealing frame and inclined side wall surfaces of a first cavity of said casing part by pressing said locking frame against said casing part until the bottom outer surface of said locking frame contacts a bottom surface of said first cavity, the latter inserting and pressing being effected by a second automatic apparatus, and (e) bonding each of said locking frames onto said bottom surface of said first cavity of said casing part.

The main advantages of a process according to the invention for assembling a plurality of chip packaging devices having the structure proposed by the instant invention are that such a process can be entirely performed using standard automated means and with a high throughput.

According to the invention the above mentioned third aim is attained with a system for carrying out evaluation and/or monitoring methods involving electro-optical reading of an active surface of a chip shaped carrier, said system comprising (a) a cartridge having an opening for introducing a liquid sample into said cartridge, said cartridge comprising a casing part, (b) said casing part having an inner surface and outer surface, a first cavity for receiving a chip shaped carrier, and means which provide visual access to said first cavity, and thereby to said active surface of said chip shaped carrier, said first cavity having a bottom surface and inclined side wall surfaces which extend either between said inner surface of said casing part and said bottom surface or between said inner surface of said casing part and said bottom surface, and which form an obtuse angle with that bottom surface, said bottom surface having an opening which opens into said second cavity, (c) a sealing frame which is part of said casing part and which is made of a compressible material, said sealing frame being connected to said bottom surface of said first cavity, (d) a locking frame, (e) the shape and dimensions of said first cavity, said chip shaped carrier, said sealing frame, said locking frame and said opening of said bottom surface of said first cavity being such that (e.1) said chip shaped carrier fits into the space delimited by said sealing frame, and a gap exists between said sealing frame and the inclined side wall surfaces of said first cavity, (e.2) said locking frame is larger than said gap, said locking frame is however insertable into said gap by pressure exerted on said locking frame against said casing part, said pressure causing a compression of said sealing frame and a corresponding pressure on a substantial part of the outer surface of the lateral periphery of said chip shaped carrier, said outer surface being in contact with said sealing frame, and (f) a chip shaped carrier having an active surface which is adapted to be read by an electro-optical reading device, said chip shaped carrier being positioned in said first cavity of said casing part.

The main advantage of a system according to the invention is that it makes possible to carry out evaluation and/or monitoring methods involving electro-optical readings of an active surface of a chip shaped carrier of the above mentioned type without the above mentioned drawbacks of prior art equipment.

BRIEF DESCRIPTION OF THE DRAWINGS

The subject invention will now be described in terms of its preferred embodiments. These embodiments are set forth to aid the understanding of the invention, but are not to be construed as limiting.

DETAILED DESCRIPTION OF THE INVENTION

First Embodiment of a Chip Packaging Device According to the Invention

Figure 1:
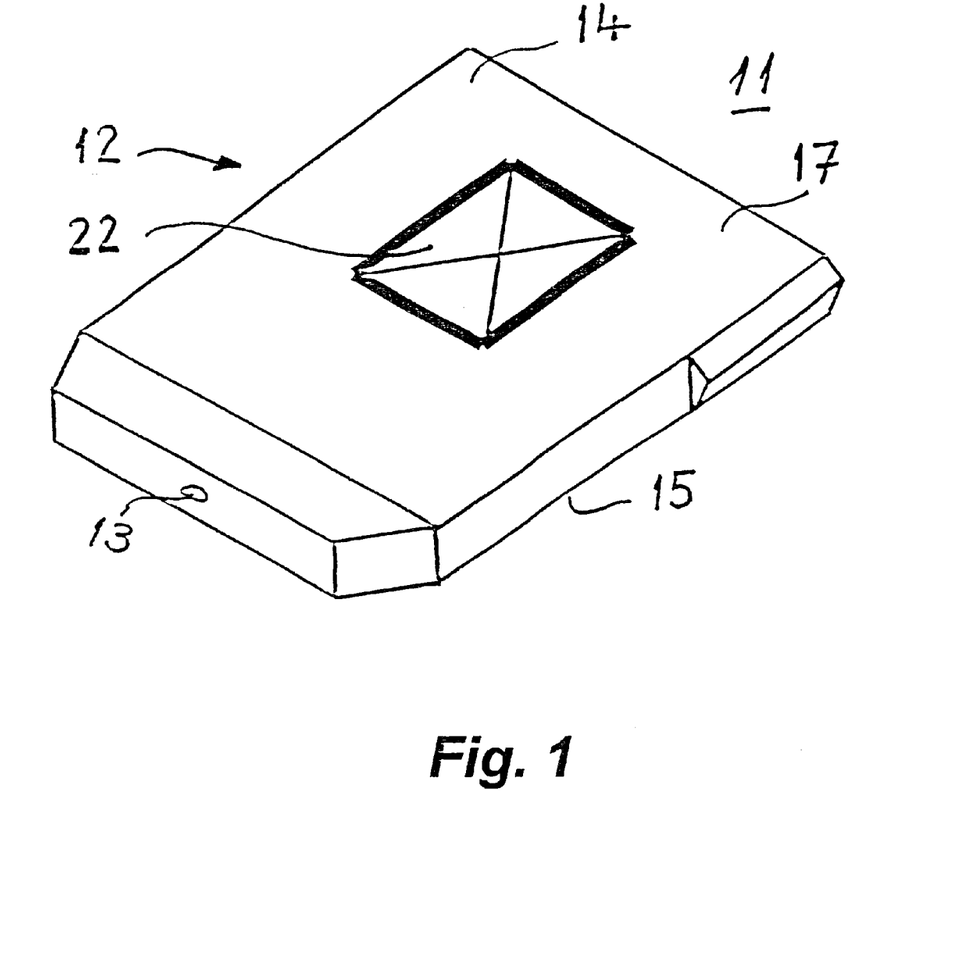
FIG. 1 shows a perspective view of a first embodiment of a chip packaging device 11 according to the invention comprising a cartridge 12.

As shown by FIG. 1 a chip packaging device 11 according to the invention comprises a cartridge 12. Cartridge 12 comprises a first casing part 14 and a second casing part 15. Casing part 15 has an opening 13 for introducing a liquid sample into cartridge 12. Casing part 15 is preferably made of an optically non-transparent material.

As can be appreciated from FIG. 2, casing part 14 has an inner surface 16 and outer surface 17, a first cavity 18 for receiving a chip shaped carrier 21—called for simplicity chip 21 hereinafter—and a second cavity 22 which forms a window providing visual access to first cavity 18, and thereby to the active surface of chip shaped carrier 21. The just described structure is just one example of means which provide visual access to that active surface. Other means which are apt to provide such access and which do not necessarily require a second cavity 22 and/or use a casing part 15 made of an optically non-transparent material will however be apparent to those skilled in the art.

The shape of cavity 22 defines the numeric aperture available for emission of fluorescence light. This aperture defines the optical accessibility of the chip which has to be guaranteed for a reading out. In the embodiment represented in FIG. 5, cavity 22 provides an aperture of 35 degrees.

Chip 21 is e.g. made of glass, has a thickness of e.g. 0.7 or 1.0 millimeter, and has substantially the shape of a square. Since the size of chip 21 has a relatively high tolerance of e.g. 0.0762 millimeter, in the embodiment described hereinafter the space available in cavity 18 for receiving and positioning chip 21 has a corresponding joint clearance.

Chip 21 has an active surface which is covered by an array 32 of oligonucleotide probes and which must not be touched at all to avoid any damage of the active surface.

Cavity 18 has a flat or substantially flat bottom surface 23 and inclined side wall surfaces 24 which extend between inner surface 16 of casing 14 and bottom surface 23. Each of the inclined side wall surfaces 24 forms an obtuse angle with bottom surface 23. Bottom surface 23 has an opening 25 which opens into second cavity 22.

Figure 2:
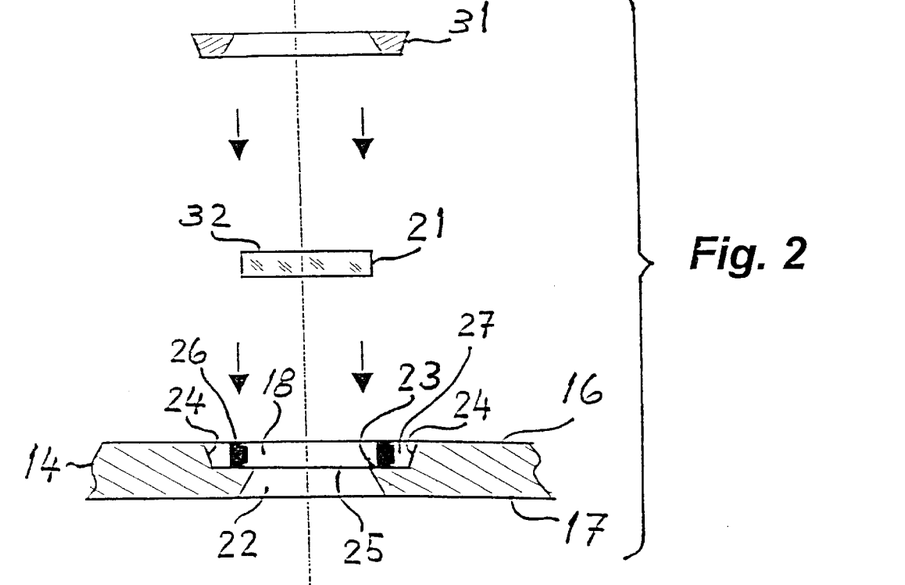
FIG. 2 shows a cross-sectional, exploded view of means used according to the invention for attaching a chip shaped carrier 21 to a first casing 14 which is part of cartridge 12 in FIG. 1.
Figure 3:
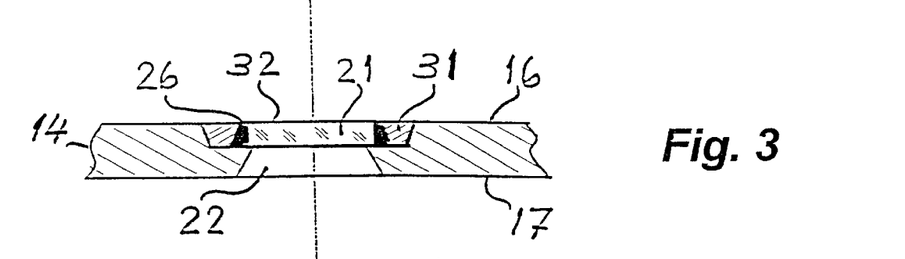
FIG. 3 shows a cross-sectional view of the means represented in FIG. 2 after they are assembled according to the invention.
Figure 5:
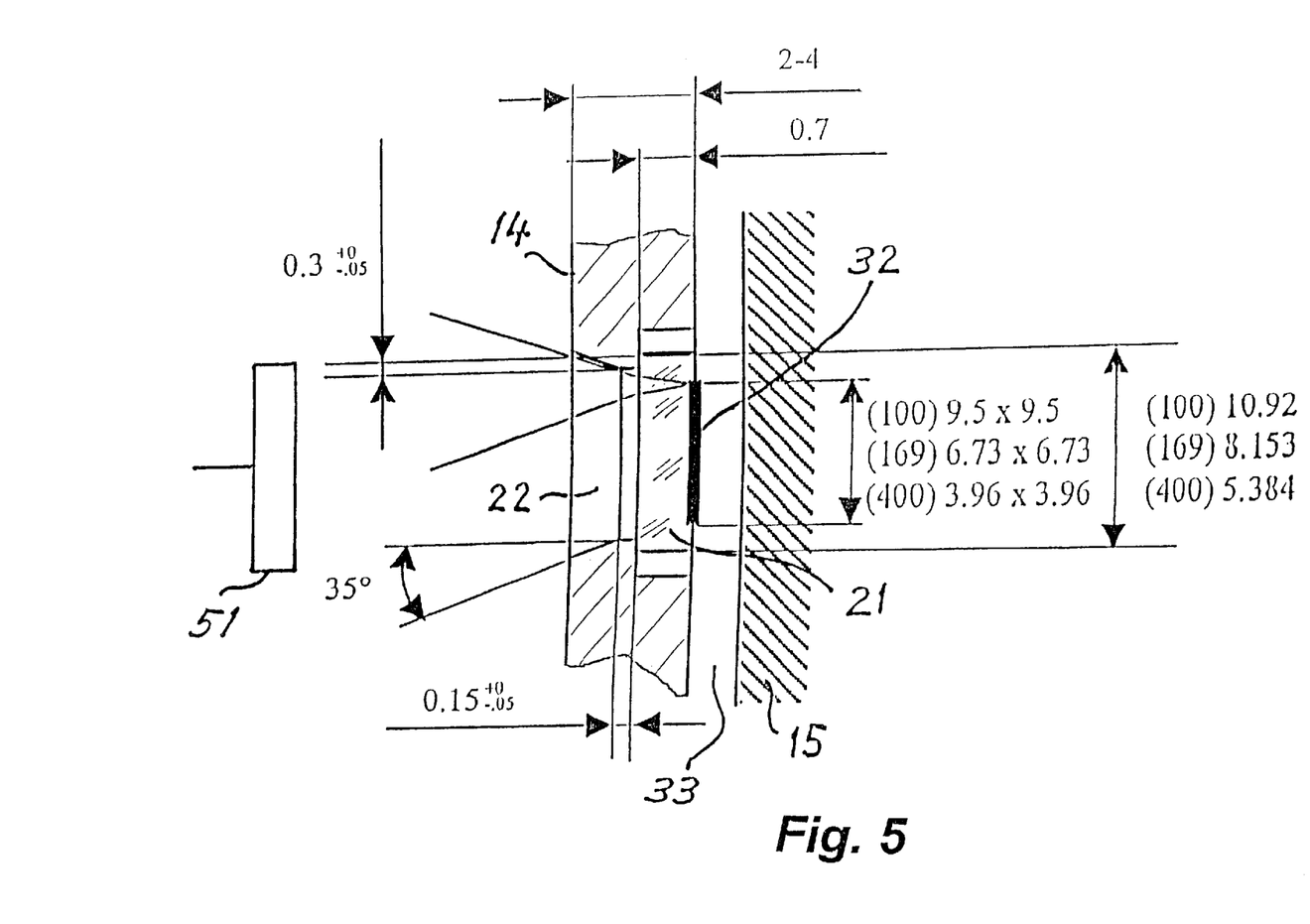
FIG. 5 shows a schematic cross-sectional view of the assembly represented in FIG. 3 and of a second casing 15 which is part of cartridge 12 in FIG. 1.

As can be appreciated in particular from FIGS. 2, 3 and 5 this first embodiment allows insertion of chip shaped carrier 21 into its position in cavity 18 from the inside of casing part 14 of cartridge 62.

A sealing frame 26, which is made of a compressible material, is part of casing 14 and is connected to bottom surface 23 of cavity 18. In a preferred embodiment, sealing frame 26 is formed onto bottom surface 23 by an injection molding process. In another embodiment sealing frame 26 is bound by adherence to bottom surface 23.

A chip packaging device according to the invention further includes a locking frame 31 represented in FIG. 2. The cross-section of locking frame 31 is wedge-shaped. In a preferred embodiment, locking frame 31 is apt to be bound to casing 14 by a welding process.

As can be appreciated from FIGS. 2 and 3, chip 21 is positioned in cavity 18 of casing part 14.

Figure 4:
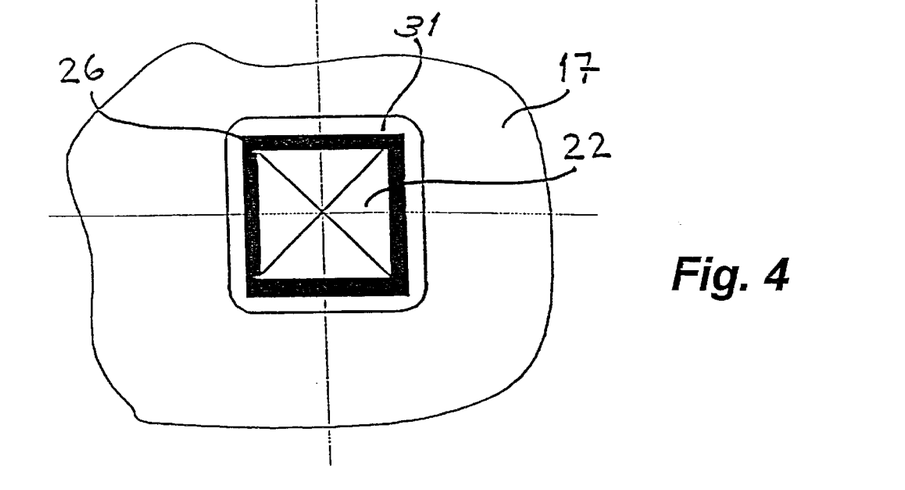
FIG. 4 shows a top view of the assembly represented in FIG. 3.

As can be appreciated from FIGS. 3 and 4, the shape and dimensions of cavity 18, chip 21, sealing frame 26, locking frame 31 and opening 25 of bottom surface 23 of cavity 18 are so chosen that chip 21 fits into the space delimited by sealing frame 26, and a gap 27 exists between sealing frame 26 and the inclined side wall surfaces 24 of first cavity 18, and locking frame 31 is larger than gap 27, but locking frame 31 is however insertable into gap 27 by a pressure exerted on locking frame 31 against casing 14. That pressure causes a compression of sealing frame 26 and a corresponding pressure on a substantial part of the outer surface of the lateral periphery of chip 21. The latter outer surface is in contact with sealing frame 26.

In a preferred embodiment, casing 14 and locking frame 31 are made of a first plastic material, e.g. a polypropylene, and sealing frame 26 is made of a second plastic material, e.g. a thermoplastic elastomer, which is softer than the first plastic material.

In a preferred embodiment part of which is schematically shown by FIG. 5, chip 21 has a first surface which is coated with a so called probe array 32, i.e. an array of diverse sequences, e.g. DNA oligonucleotides, located at known positions on that first surface, a second surface opposite to the first surface, and a third surface which extends between the first and second surfaces, is normal to these surfaces, and is the outer surface of the lateral periphery of chip 21.

Since the active coating 32 of chip 21, that is the surface thereof of which is coated with the above mentioned diverse sequences, has to be accessible e.g. to optical detection means 51, e.g. for performing fluorescence measurements, chip 21 is inserted into the outer wall of cartridge 12, and its active coating 32 faces the interior of a so-called process chamber 33 within cartridge 12.

As can be appreciated from FIG. 5, second cavity 22 forms a window which provides visual access to the active surface of chip shaped carrier 21. The just described structure is just one example of means which provide visual access to that active surface. Other means which are apt to provide such access and which do not necessarily require a cavity 22 and/or use a casing part 15 made of an optically non-transparent material will however be apparent to those skilled in the art.

The geometric specifications of mounting of chip 21 are represented in FIG. 5, where all dimensions are indicated in millimeters. As indicated therein, chip 21 can have three sizes designated by numbers 100, 169 and 400. Chip size 100 has a square side length of 10.92 millimeters. Chip size 169 has a square side length of 8.153 millimeters. Chip size 400 has a square side length of 5.384 millimeters. The active surface of chip size 100 has a square side length of 9.5 millimeters. The active surface of chip size 169 has a square side length of 6.73 millimeters. The active surface of chip size 400 has a square side length of 3.96 millimeters.

As can be appreciated from FIG. 5, the above described means for attaching chip 21 to casing part 14 make it possible to mount chip 21 so that it is coplanar with the side of casing 14 which faces processing chamber 33.

Since the chip is only held by friction forces, a minimum chip contact force of 5N has been defined to ensure proper operation, and in particular to ensure that the chip mounting remain liquid-tight up to an overpressure of 300 millibar.

Second Embodiment of a Chip Packaging Device According to the Invention

Figure 6:
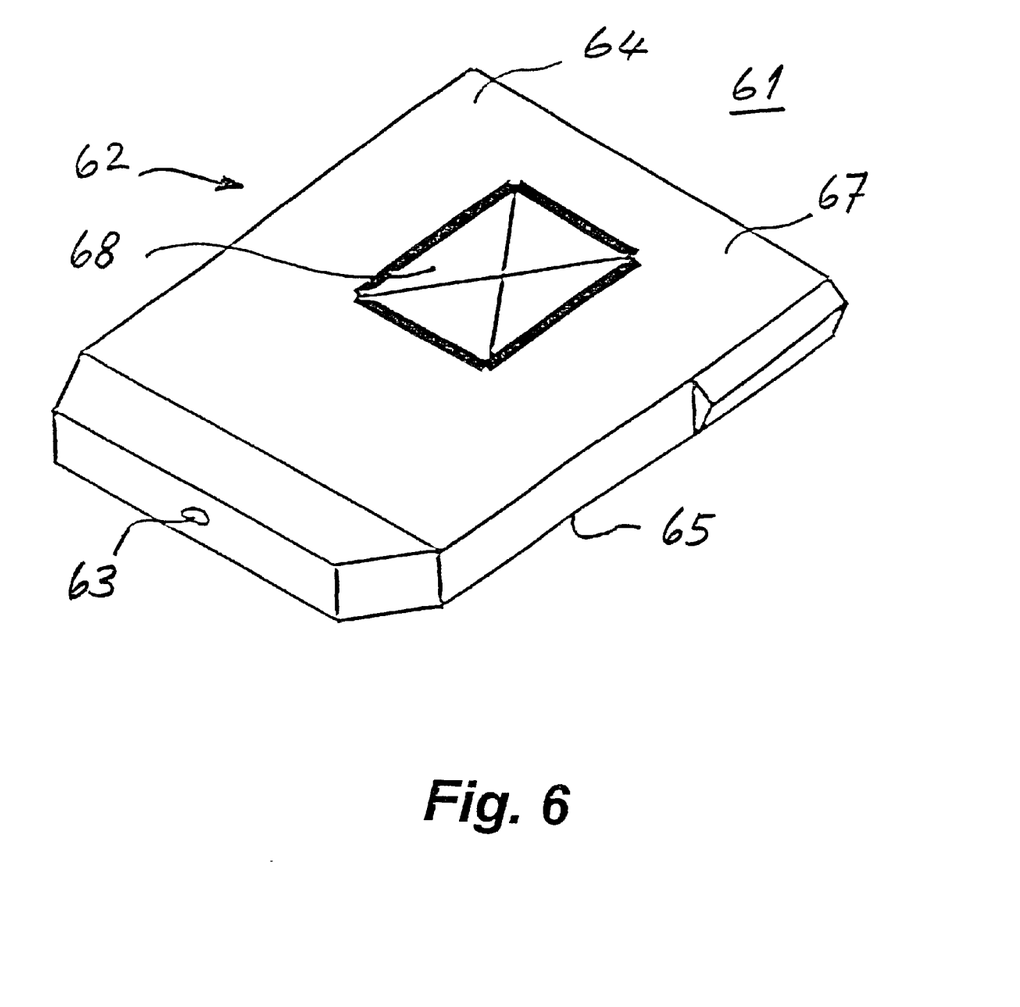
FIG. 6 shows a perspective view of a second embodiment of a chip packaging device 61 according to the invention comprising a cartridge 62.

As shown by FIG. 6 a chip packaging device 61 according to the invention comprises a cartridge 62. Cartridge 62 comprises a first casing part 64 and a second casing part 65. Casing part 65 has an opening 63 for introducing a liquid sample into cartridge 62. Casing part 65 is preferably made of an optically non-transparent material.

As can be appreciated from FIG. 7, casing part 64 has an inner surface 66 and outer surface 67, a first cavity 68 for receiving a chip shaped carrier 21—called for simplicity chip 21 hereinafter—and a second cavity 78 which faces the interior of a so-called process chamber 83 within cartridge 62. Process chamber 83 is represented in FIG. 10.

Figure 8:
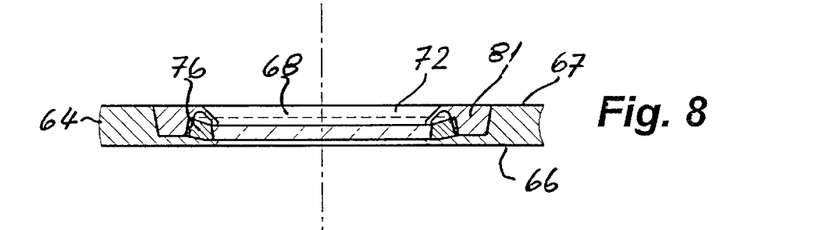
FIG. 8 shows a cross-sectional view of the means represented in FIG. 7 after they are assembled according to the invention.
Figure 10:
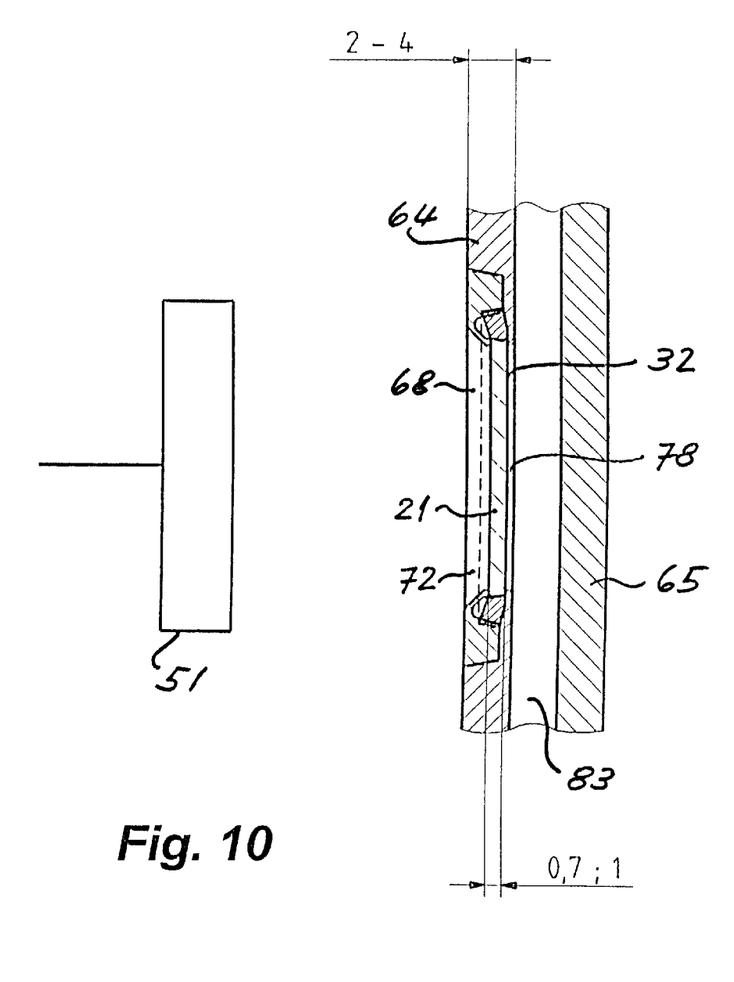
FIG. 10 shows a schematic cross-sectional view of the assembly represented in FIG. 7 and of a second casing 65 which is part of cartridge 62 in FIG. 6.

The shape of cavity 72, which as shown in FIG. 8 and FIG. 10 lies between chip shaped carrier 21 and the plane defined by outer surface 67, defines the numeric aperture available for emission of fluorescence light. This aperture defines the optical accessibility of the chip which has to be guaranteed for a reading out.

Chip 21 is e.g. made of glass, has a thickness of e.g. 0.7 or 1.0 millimeter, and has substantially the shape of a square. Since the size of chip 21 has a relatively high tolerance of e.g. 0.0762 millimeter, in the embodiment described hereinafter the space available in cavity 68 for receiving and positioning chip 21 has a corresponding joint clearance.

Chip 21 has an active surface which is covered by an array 32 of oligonucleotide probes and which must not be touched at all to avoid any damage of the active surface.

Cavity 68 has a flat or substantially flat bottom surface 73 and inclined side wall surfaces 74 which extend between outer surface 67 of casing 64 and bottom surface 73. Each of the inclined side wall surfaces 74 forms an obtuse angle with bottom surface 73. Bottom surface 73 has an opening 75 which opens into second cavity 72.

Figure 7:
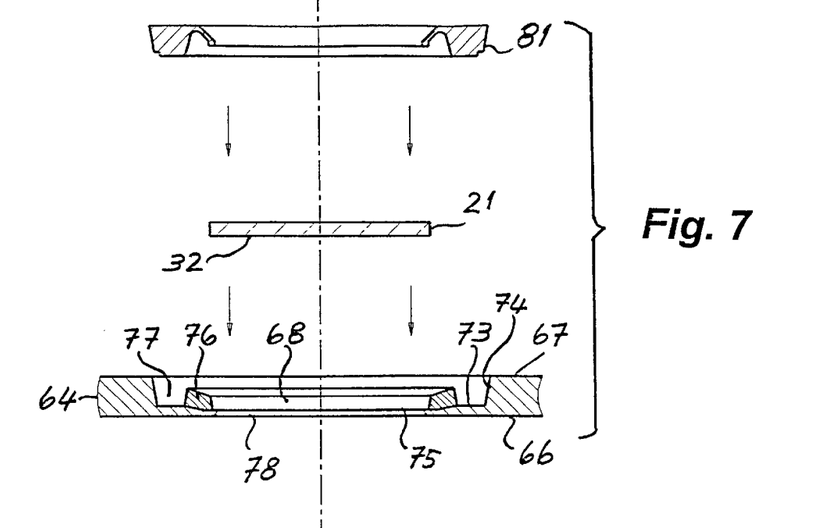
FIG. 7 shows a cross-sectional, exploded view of means used according to the invention for attaching a chip shaped carrier 21 to a first casing 64 which is part of cartridge 62 in FIG. 6.

As can be appreciated in particular from FIGS. 7, 8 and 19 this second embodiment offers the advantage that it allows insertion of chip shaped carrier 21 into its position in cavity 68 from the outside of cartridge 62. This is advantageous for an automatic assembling of chip packaging devices according to the invention.

A sealing frame 76, which is made of a compressible material, is part of casing 64 and is connected to bottom surface 73 of cavity 68. In a preferred embodiment, sealing frame 76 is formed onto bottom surface 73 by an injection molding process. In another embodiment sealing frame 76 is bound by adherence to bottom surface 73.

A chip packaging device according to the invention further includes a locking frame 81 represented in FIG. 7. The cross-section of locking frame 81 is wedge-shaped. In a preferred embodiment, locking frame 81 is apt to be bound to casing 64 by a welding process.

As can be appreciated from FIGS. 7 and 8, chip 21 is positioned in cavity 68 of casing part 64.

Figure 9:
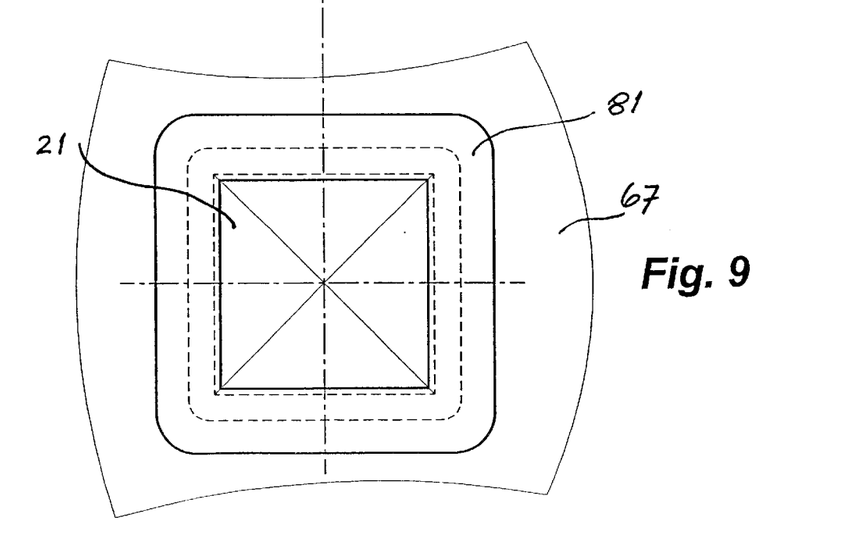
FIG. 9 shows a top view of the assembly represented in FIG. 7.

As can be appreciated from FIGS. 8 and 9, the shape and dimensions of cavity 68, chip 21, sealing frame 76, locking frame 81 and opening 75 of bottom surface 73 of cavity 68 are so chosen that chip 21 fits into the space delimited by sealing frame 76, and a gap 77 exists between sealing frame 76 and the inclined side wall surfaces 74 of first cavity 68, and locking frame 81 is larger than gap 77, but locking frame 81 is however insertable into gap 77 by a pressure exerted on locking frame 81 against casing 64. That pressure causes a compression of sealing frame 76 and a corresponding pressure on a substantial part of the outer surface of the lateral periphery of chip 21. The latter outer surface is in contact with sealing frame 76.

In a preferred embodiment, casing 64 and locking frame 81 are made of a first plastic material, e.g. a polypropylene, and sealing frame 76 is made of a second plastic material, e.g. a thermoplastic elastomer, which is softer than the first plastic material.

In a preferred embodiment part of which is schematically shown by FIG. 10, chip 21 has a first surface which is coated with a so called probe array 32, i.e. an array of diverse sequences, e.g. DNA oligonucleotides, located at known positions on that first surface, a second surface opposite to the first surface, and a third surface which extends between the first and second surfaces, is normal to these surfaces, and is the outer surface of the lateral periphery of chip 21.

Since the active coating 32 of chip 21, that is the surface thereof of which is coated with the above mentioned diverse sequences, has to be accessible e.g. to optical detection means 51, e.g. for performing fluorescence measurements, chip 21 is inserted into the outer wall of cartridge 62, and its active coating 32 faces the interior of process chamber 83 within cartridge 62.

As can be appreciated from FIG. 10, cavity 72 forms a window which provides visual access to the active surface of chip shaped carrier 21. The just described structure is just one example of means which provide visual access to that active surface. Other means which are apt to provide such access and which do not necessarily require a cavity 72 and/or use a casing part 65 made of an optically non-transparent material will however be apparent to those skilled in the art.

The geometric specifications of mounting of chip 21 are similar to those represented in and described with reference to FIG. 5.

As can be appreciated from FIG. 10, the above described means for attaching chip 21 to casing part 64 make it possible to mount chip 21 so that it is nearly coplanar with the side of casing 64 which faces processing chamber 83.

Since the chip is only held by friction forces, a minimum chip contact force of 5N has been defined to ensure proper operation, and in particular to ensure that the chip mounting remain liquid-tight up to an overpressure of 300 millibar.

A further aspect of the invention relates to a process for an automated assembling a plurality of chip packaging devices according to the invention.

Figure 11:
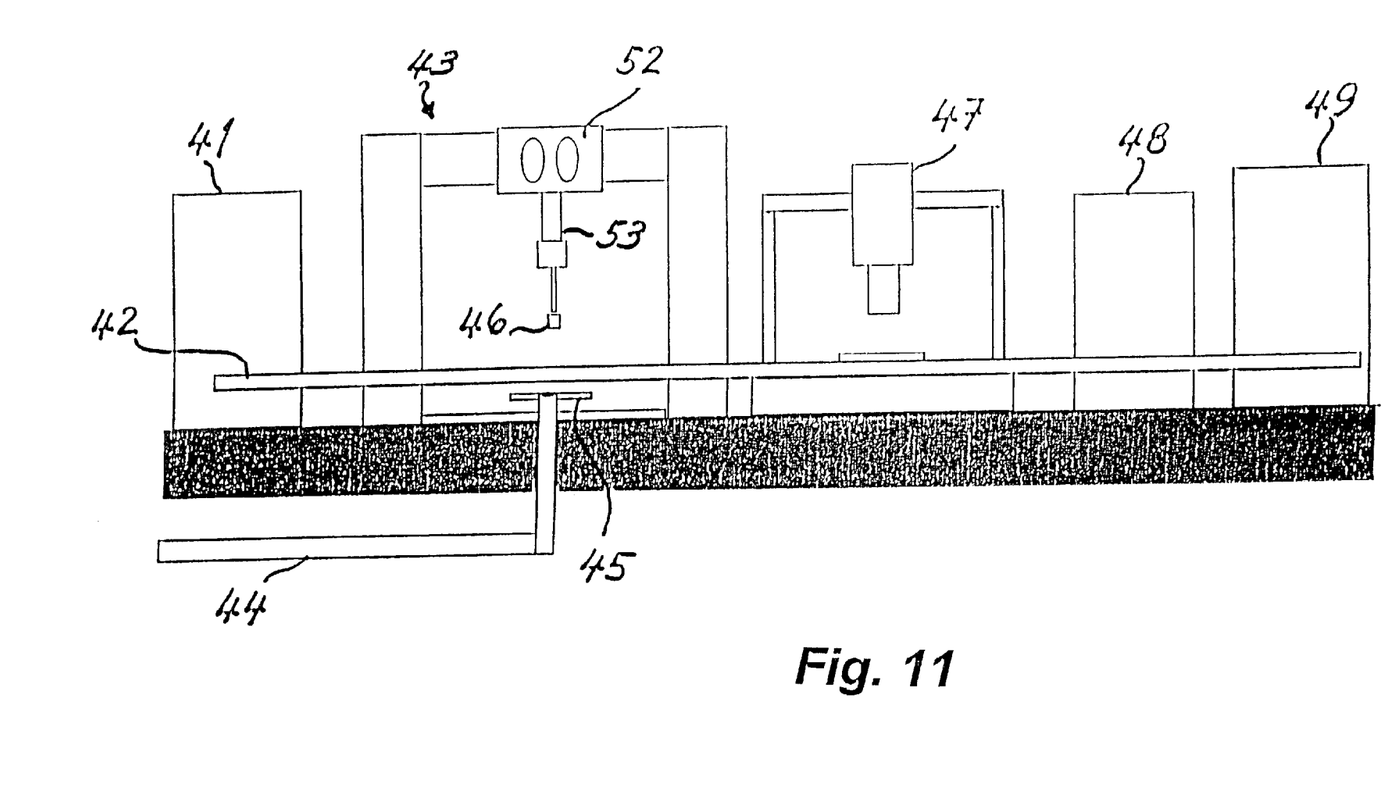
FIG. 11 shows an assembly line for automatically packaging chips in cartridges.

Example of an Assembly Line For Automated Assembling of a Plurality of Chip Packaging Devices According to the Invention FIG. 11 schematically shows the structure of an completely automatic assembly line for carrying out such a process. This assembly line comprises a stock 41 of casing parts 14, 15 of cartridges 12 (described above with reference to FIGS. 1–5) or of casing parts 64, 65 of cartridges 62 (described above with reference to FIGS. 6–10), a first conveyor 42, a die bonder 43, a second conveyor 44 for conveying blue tapes which come from a diamond saw cutting machine and which carry a plurality of chip shaped carriers 21, an ultrasonic welding machine 47, an automatic packing apparatus 48, and a stack of completely assembled chip packaging devices 49. Assembly line components 42 to 48 are all standard apparatuses and devices suitable for automated operation. Die bonder 43 comprises a blue tape support 45 having an expansion mechanism, a working frame 52 movable in x- and y-direction and a tool holder 53 which holds a die collect 46. Tool holder 53 is connected to working frame 52 and is thereby movable in x- and y-direction. Tool holder 53 has a spindle which enables to move die collect 46 in z-direction.

First Example of a Process For Assembling a Plurality of Chip Packaging Devices According to the Invention According to the invention a process for assembling a plurality of chip packaging devices 11 described above with reference to FIGS. 1 to 5 comprises the following steps:

(a) providing to an input side of the automatic assembly line shown by FIG. 11 a plurality of casings 14 and a plurality of locking frames 31, each of casings 14 comprising a sealing frame 26 which is formed thereon e.g. by an injection molding process, (b) providing a plurality of chip shaped carriers 21 each of which has an active surface 32 to the assembly line, (c) positioning each of carriers 21 within a sealing frame 26 of one of the casing parts 14 by means of automatic die bonder 43, (d) inserting each of locking frames 31 into gap 27 between the sealing frame 26 and the inclined side wall surfaces 24 of a cavity 18 of the casing part 14 by pressing it against that casing part 14 until the bottom outer surface of locking frame 31 contacts bottom surface 23 of that cavity 18, the latter inserting and pressing being effected by an automatic apparatus, e.g. by ultrasonic welding machine 47, and (e) bonding each of the inserted locking frames 31 onto the bottom surface 23 of the first cavity 18 of the casing part 14.

In the above mentioned process steps (a) and (b) casings 14 and a locking frames 31 are preferably transferred one-by-one via first conveyor 42 from stock of parts 41 to die bonder 43 and from there successively to the other parts of the assembly line where a processing step has to be carried out. In a similar way and with a proper timing chip shaped carriers 21 are also transferred one-by-one via second conveyor 44 and blue tape support 45 to die bonder 43.

In all above mentioned process steps, the active surface of chip 21 is not touched at all, and this ensures that no damage of that active surface can take place during the assembling process. In addition, the above defined process ensures that the quality of the cutting of chip 21 remains basically unchanged.

In a preferred embodiment, each locking frame 31 is bond onto one of casing parts 14 by a welding process, and preferably by an ultrasonic welding process.

In a further preferred embodiment, at least the following of the above mentioned assembling steps are carried out in a clean room:

positioning each of the carriers 21 within one of the sealing frames 26, inserting each of the locking frames 31 into one of the gaps 27, and welding each of the locking frames 31 onto one of the casings 14.

After bonding of a locking frame 31 to a casing part 14, this casing part and a complementary casing part 15 are provided to an automatic packaging apparatus 48, where both casing parts 14 and 15 are put together to form a complete chip packaging device 11, that is a cartridge 12 containing a chip shaped carrier 21.

An outstanding advantage of the device and the assembling process according to the invention is that they allow adjustment of the lateral insertion clearance when inserting the chip in cavity 18 of casing part 14. This adjustment possibility eliminates on the one hand the need for a highly accurate positioning of chip 21 in its mounting and the need for relatively large forces for effecting that mounting, and on the other hand allows the use of commercially available standard appliances used for the automated manufacture of integrated circuits.

An example of such a standard appliance is e.g. a die bonder which can supply a maximum joining force of 10 Newton. A die bonder is typically used for bonding an electronic silicon chip on a so-called lead frame. Afterwards, the copper lead frame and the silicon chip are electrically connected by means of gold wires. In the above described assembling process such a die bonder is used in a first step for inserting the chips 21 into cavity 18 of casing part 14 of cartridge 12. In a second step, locking frame 31 is welded in ultrasonic welding machine 47 to casing part 14.

The advantage of such an automated assembly line is that it makes possible to use a mounting machine suitable for use in a clean-room, namely the die bonder, in which the removal of chip 21 from a so-called "blue tape" is already integrated. The minimization of the joining force used for bonding chip 21 and casing part 14 is supported by a vision system.

An essential feature of a chip packaging device according to the invention and the process according to the invention for assembling such a device is that chip 21 is held in its position within cavity 18 exclusively by lateral forces applied on the peripheral surface of chip 21 which is in contact with sealing frame 26.

Second Example of a Process For Assembling a Plurality of Chip Packaging Devices According to the Invention According to the invention a process for assembling a plurality of chip packaging devices 61 described above with reference to FIGS. 6 to 10 comprises the following steps:

(a) providing to an input side of the automatic assembly line shown by FIG. 11 a plurality of casings 64 and a plurality of locking frames 81, each of casings 64 comprising a sealing frame 76 which is formed thereon e.g. by an injection molding process, (b) providing a plurality of chip shaped carriers 21 each of which has an active surface 32 to the assembly line, (c) positioning each of carriers 21 within a sealing frame 76 of one of the casing parts 64 by means of automatic die bonder 43, (d) inserting each of locking frames 81 into gap 77 between the sealing frame 76 and the inclined side wall surfaces 74 of a cavity 68 of the casing part 64 by pressing it against that casing part 64 until the bottom outer surface of locking frame 81 contacts bottom surface 73 of that cavity 68, the latter inserting and pressing being effected by an automatic apparatus, e.g. by ultrasonic welding machine 47,and (e) bonding each of the inserted locking frames 81 onto the bottom surface 73 of the first cavity 68 of the casing part 64.

In the above mentioned process steps (a) and (b) casings 64 and a locking frames 81 are preferably transferred one-by-one via first conveyor 42 from stock of parts 41 to die bonder 43 and from there successively to the other parts of the assembly line where a processing step has to be carried out. In a similar way and with a proper timing chip shaped carriers 21 are also transferred one-by-one via second conveyor 44 and blue tape support 45 to die bonder 43.

In all above mentioned process steps, the active surface of chip 21 is not touched at all, and this ensures that no damage of that active surface can take place during the assembling process. In addition, the above defined process ensures that the quality of the cutting of chip 21 remains basically unchanged.

In a preferred embodiment, each locking frame 81 is bond onto one of casing parts 64 by a welding process, and preferably by an ultrasonic welding process.

In a further preferred embodiment, at least the following of the above mentioned assembling steps are carried out in a clean room:

positioning each of the carriers 21 within one of the sealing frames 76, inserting each of the locking frames 81 into one of the gaps 77, and welding each of the locking frames 81 onto one of the casings 64.

After bonding of a locking frame 81 to a casing part 64, this casing part and a complementary casing part 65 are provided to an automatic packaging apparatus 48, where both casing parts 64 and 65 are put together to form a complete chip packaging device 61, that is a cartridge 62 containing a chip shaped carrier 21.

An outstanding advantage of the device and the assembling process according to the invention is that they allow adjustment of the lateral insertion clearance when inserting the chip in cavity 68 of casing part 64. This adjustment possibility eliminates on the one hand the need for a highly accurate positioning of chip 21 in its mounting and the need for relatively large forces for effecting that mounting, and on the other hand allows the use of commercially available standard appliances used for the automated manufacture of integrated circuits.

An example of such a standard appliance is e.g. a die bonder which can supply a maximum joining force of 10 Newton. A die bonder is typically used for bonding an electronic silicon chip on a so-called lead frame. Afterwards, the copper lead frame and the silicon chip are electrically connected by means of gold wires. In the above described assembling process such a die bonder is used in a first step for inserting the chips 21 into cavity 68 of casing part 64 of cartridge 62. In a second step, locking frame 81 is welded in ultrasonic welding machine 47 to casing part 64.

The advantage of such an automated assembly line is that it makes possible to use a mounting machine suitable for use in a clean-room, namely the die bonder, in which the removal of chip 21 from a so-called "blue tape" is already integrated. The minimization of the joining force used for bonding chip 21 and casing part 64 is supported by a vision system.

An essential feature of a chip packaging device according to the invention and the process according to the invention for assembling such a device is that chip 21 is held in its position within cavity 68 exclusively by lateral forces applied on the peripheral surface of chip 21 which is in contact with sealing frame 76.

First Example of a System According to the Invention For Carrying Out Evaluation and/or Monitoring Methods Involving Electro-Optical Reading of an Active Surface of a Chip Shaped Carrier Such a system comprises a chip packaging device as described above with reference to FIGS. 1 to 5 and is useful for carrying out evaluation and/or monitoring methods involving electro-optical reading of an active surface of a chip shaped carrier. According to the invention such a system comprises (a) a cartridge 12 having an opening 13 for introducing a liquid sample into the cartridge 12, the cartridge 12 comprising a casing part 14, (b) casing part 14 has an inner surface 16 and outer surface 17, a first cavity 18 for receiving a chip shaped carrier 21, and means 22 which provide visual access to first cavity 18, and thereby to the active surface of chip shaped carrier 21, first cavity 18 has a bottom surface 23 and inclined side wall surfaces 24 which extend between the inner surface 16 of the casing part 14 and the bottom surface 23 and which form an obtuse angle with that bottom surface 23, (c) a sealing frame 26 which is part of casing part 14 and which is made of a compressible material, sealing frame 26 is connected to bottom surface 23 of first cavity 18, (d) a locking frame 31, (e) the shape and dimensions of first cavity 18, chip shaped carrier 21, sealing frame 26, and locking frame 31 are such that (e.1) chip shaped carrier 21 fits into the space delimited by the sealing frame 26, and a gap 27 exists between the sealing frame 26 and the inclined side wall surfaces 24 of first cavity 18, (e.2) locking frame 31 is larger than gap 27, locking frame 31 is however insertable into gap 27 by pressure exerted on locking frame 31 against casing part 14, that pressure causing a compression of sealing frame 26 and a corresponding pressure on a substantial part of the outer surface of the lateral periphery of chip shaped carrier 21, that outer surface being in contact with sealing frame 26, and (f) a chip shaped carrier 21 having an active surface which is adapted to be read by an electro-optical reading device, and chip shaped carrier is positioned in first cavity 18 of casing part 14.

In a preferred embodiment the above described system further comprises electro-optically reading means 51, schematically represented in FIG. 5, for reading the active surface 32 of chip shaped carrier 21. Electro-optically reading means 51 can be e.g. a fluorometer, that is an apparatus comprising a light source for irradiating active surface 32 with an excitation beam, light detection means for detecting fluorescent light emitted e.g. by a probe array forming part of active surface and providing a corresponding output signal, 32 and means for evaluating and/or monitoring that output signal.

Second Example of a System According to the Invention For Carrying Out Evaluation and/or Monitoring Methods Involving Electro-Optical Reading of an Active Surface of a Chip Shaped Carrier Such a system comprises a chip packaging device as described above with reference to FIGS. 6 to 10 and is useful for carrying out evaluation and/or monitoring methods involving electro-optical reading of an active surface of a chip shaped carrier. According to the invention such a system comprises (a) a cartridge 62 having an opening 63 for introducing a liquid sample into the cartridge 62, the cartridge 62 comprising a casing part 64, (b) casing part 64 has an inner surface 66 and outer surface 67, a first cavity 68 for receiving a chip shaped carrier 21, and means 72 which provide visual access to first cavity 68, and thereby to the active surface of chip shaped carrier 21, first cavity 68 has a bottom surface 73 and inclined side wall surfaces 74 which extend between the inner surface 66 of the casing part 64 and the bottom surface 73 and which form an obtuse angle with that bottom surface 73, (c) a sealing frame 76 which is part of casing part 64 and which is made of a compressible material, sealing frame 76 is connected to bottom surface 73 of first cavity 68, (d) a locking frame 81, (e) the shape and dimensions of first cavity 68, chip shaped carrier 21, sealing frame 76, and locking frame 81 are such that (e.1) chip shaped carrier 21 fits into the space delimited by the sealing frame 76, and a gap 77 exists between the sealing frame 76 and the inclined side wall surfaces 74 of first cavity 68, (e.2) locking frame 81 is larger than gap 77, locking frame 81 is however insertable into gap 77 by pressure exerted on locking frame 81 against casing part 64, that pressure causing a compression of sealing frame 76 and a corresponding pressure on a substantial part of the outer surface of the lateral periphery of chip shaped carrier 21, that outer surface being in contact with sealing frame 76, and (f) a chip shaped carrier 21 having an active surface which is adapted to be read by an electro-optical reading device, and chip shaped carrier is positioned in first cavity 68 of casing part 64.

In a preferred embodiment the above described system further comprises electro-optically reading means 51, schematically represented in FIG. 10, for reading the active surface 32 of chip shaped carrier 21. Electro-optically reading means 51 can be e.g. a fluorometer, that is an apparatus comprising a light source for irradiating active surface 32 with an excitation beam, light detection means for detecting fluorescent light emitted e.g. by a probe array forming part of active surface and providing a corresponding output signal, 32 and means for evaluating and/or monitoring that output signal.

Modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus may be varied without departing from the spirit of the invention and the exclusive use of all modifications which come within the scope of the appended claims is reserved.

List of Reference Numbers
11 chip packaging device
12 cartridge
13 opening of cartridge
14 first casing part
15 second casing part
16 inner surface of casing 14
17 outer surface of casing 14
18 first cavity of casing 14
21 chip shaped carrier
22 second cavity of casing 14
23 bottom surface of first cavity 18 of casing 14
24 inclined side wall surfaces of first cavity 18
25 opening of bottom surface 23
26 sealing frame
27 gap
31 locking frame
32 probe array on a first surface of chip shaped carrier 21
33 processing chamber
41 stock of empty parts
42 first conveyor
43 die-bonder
44 second conveyor
45 blue tape support
46 die collect
47 welding machine
48 packing apparatus
49 stack
51 electro-optical reading means
52 working frame
53 tool holder
61 chip packaging device
62 cartridge
63 opening of cartridge
64 first casing part
65 second casing part
66 inner surface of casing 64
67 outer surface of casing 64
68 first cavity of casing 64
72 cavity of casing 64
73 bottom surface of first cavity 68 of casing 64
74 inclined side wall surfaces of first cavity 68
75 opening of bottom surface 73
76 sealing frame
77 gap
78 second cavity of casing 64
81 locking frame
83 processing chamber

What is claimed is:

1. A device for packaging a chip shaped carrier having an active surface which is adapted to be read by an electro-optical reading device, said device comprising (a) a cartridge having a processing chamber and an opening for introducing a liquid sample into said processing chamber, said cartridge comprising a casing part, (b) said casing part having an inner surface which faces said processing chamber and an outer surface, a first cavity for receiving a chip shaped carrier, and means which provide visual access to said first cavity, and thereby to said active surface of said chip shaped carrier,
  said first cavity having a bottom surface and inclined side wall surfaces which extend between said outer surface of said casing part and said bottom surface and which form an obtuse angle with that bottom surface,
(c) a sealing frame which is part of said casing part and which is made of a compressible material, said sealing frame being connected to said bottom surface of said first cavity, and
(d) a locking frame,
(e) the shape and dimensions of said first cavity, said chip shaped carrier, said sealing frame, and said locking frame, being such that
  (e.1) said chip shaped carrier fits into the space delimited by said sealing frame, and a gap, exists between said sealing frame and the inclined side wall surfaces of said first cavity,
  (e.2) said locking frame, is larger than said gap, said locking frame is however insertable into said gap, by pressure exerted on said locking frame against said casing part, said pressure causing a compression of said sealing frame and a corresponding pressure on a substantial part of the outer surface of the lateral periphery of said chip shaped carrier, said outer surface of said chip shaped carrier being in contact with said sealing frame.

2. The chip packaging device according to claim 1, wherein said casing part and said locking frame are made of a first plastic material, and said sealing frame is made of a second plastic material, said second plastic material being softer than said first plastic material.

3. The chip packaging device according to claim 2, wherein said first plastic material is a polypropylene and said second plastic material is a thermoplastic elastomer.

4. The chip packaging device according to claim 1, wherein said locking frame is apt to be bound to said casing part by a welding process.

5. The chip packaging device according to claim 1, wherein the cross-section of said locking frame is wedge-shaped.

6. The chip packaging device according to claim 1, wherein said sealing frame is formed onto said bottom surface by an injection molding process.

7. The chip packaging device according to claim 1, wherein said sealing frame is bound by adherence to said bottom surface.

8. The chip packaging device according to claim 1, wherein said chip shaped carrier is made of glass and has a surface having substantially the shape of a square.

9. The chip packaging device according to claim 1, wherein said chip shaped carrier has a first surface comprising a probe array, a second surface opposite to said first surface, and a third surface which extends between said first and second surfaces, is normal to these surfaces, and is the outer surface of the lateral periphery of said carrier, said carrier being positioned in said first cavity of said casing part such that said probe array faces said processing chamber.

10. The chip packaging device according to claim 1, wherein said means which provide visual access to said first cavity comprise a second cavity which forms a window adapted to provide said visual access, said second cavity being formed in said inner surface of said casing part.

11. A process for assembling a plurality of chip packaging devices according to claim 1 comprising (a) providing a plurality of said cartridges and a plurality of said locking frames to an automated assembly line,
(b) providing a plurality of chip shaped carriers having each an active surface to said assembly line,
(c) positioning each of said chip shaped carriers within said sealing frame of one of said cartridges by means of a first automatic apparatus,
(d) inserting each of said locking frames into said gap between said sealing frame and said inclined side wall surfaces of said first cavity of said casing part: by pressing said locking frame against said casing part until the bottom outer surface of said locking frame contacts a bottom surface of said first cavity, the latter inserting and pressing being effected by a second automatic apparatus, and
(e) bonding each of said locking frames onto said bottom surface of said first cavity of said casing part.

12. The process according to claim 11, wherein each of said locking frames is bond onto one of said casing parts by a welding process.

13. The process according to claim 12, wherein said welding process for bonding said inserted locking frame onto said casing part is an ultrasonic welding process.

14. The process according to claim 11, wherein each of said casing parts is manufactured by a first injection molding process with a first plastic material, and said bounding of each of said sealing frames to a corresponding casing part is effected by a second injection molding process with a second plastic material.

15. The process according to claim 11, wherein said second plastic material is softer than said first plastic material.

16. A device for packaging a chip shaped carrier having an active surface which is adapted to be read by an electro-optical reading device, said device comprising
(a) a cartridge having a processing chamber and an opening for introducing a liquid sample into said processing chamber, said cartridge comprising a casing part,
(b) said casing part having an inner surface which faces said processing chamber and an outer surface, a first cavity for receiving a chip shaped carrier, and means which provide visual access to said first cavity, and thereby to said active surface of said chip shaped carrier,
  said first cavity having a bottom surface and inclined side wall surfaces which extend between said inner surface of said casing part and said bottom surface and which form an obtuse angle with that bottom surface,
(c) a sealing frame which is part of said casing part and which is made of a compressible material, said sealing frame being connected to said bottom surface of said first cavity, and
(d) a locking frame,
(e) the shape and dimensions of said first cavity, said chip shaped carrier, said sealing frame, and said locking frame being such that
  (e.1) said chip shaped carrier fits into the space delimited by said sealing frame and a gap, exists between said sealing frame and the inclined side wall surfaces of said first cavity,
  (e.2) said locking frame is larger than said gap, said locking frame, is however insertable into said gap by pressure exerted on said locking frame against said casing part, said pressure causing a compression of said sealing frame and a corresponding pressure on a substantial part of the outer surface of the lateral periphery of said chip shaped carrier, said outer surface of said ship shaped carrier being in contact with said sealing frame.

17. The chip packaging device according to claim 16, wherein said casing part and said locking frame are made of a first plastic material, and said sealing frame is made of a second plastic material, said second plastic material being softer than said first plastic material.

18. The chip packaging device according to claim 17, wherein said first plastic material is a polypropylene and said second plastic material is a thermoplastic elastomer.

19. The chip packaging device according to claim 16, wherein said locking frame is apt to be bound to said casing part by a welding process.

20. The chip packaging device according to claim 16, wherein the cross-section of said locking frame is wedge-shaped.

21. The chip packaging device according to claim 16, wherein said sealing frame is formed onto said bottom surface by an injection molding process.

22. The chip packaging device according to claim 16, wherein said sealing frame is bound by adherence to said bottom surface.

23. The chip packaging device according to claim 16, wherein said chip shaped carrier is made of glass and has a surface having substantially the shape of a square.

24. The chip packaging device according to claim 16, wherein said chip shaped carrier has a first surface comprising a probe array, a second surface opposite to said first surface, and a third surface which extends between said first and second surfaces, is normal to these surfaces, and is the outer surface of the lateral periphery of said carrier, said carrier being positioned in said first cavity of said casing part such that said probe array faces said processing chamber.

25. The chip packaging device according to claim 16, wherein said means which provide visual access to said first cavity comprise a second cavity which forms a window adapted to provide said visual access, said second cavity being formed in said inner surface of said casing part.

26. A process for assembling a plurality of chip packaging devices according to claim 16 comprising
(a) providing a plurality of said cartridges and a plurality of said locking frames to an automated assembly line,
(b) providing a plurality of chip shaped carriers, having each an active surface to said assembly line,
(c) positioning each of said chip shaped carriers within said sealing frame of one of said cartridges by means of a first automatic apparatus,
(d) inserting each of said locking frames into said gap between said sealing frame and said inclined side wall surfaces of said first cavity of said casing part by pressing said locking frame against said casing part until the bottom outer surface of said locking frame contacts a bottom surface of said first cavity, the latter inserting and pressing being effected by a second automatic apparatus, and
(e) bonding each of said locking frames onto said bottom surface of said first cavity of said casing part.

27. The process according to claim 26, wherein each of said locking frames is bond onto one of said casing parts by a welding process.

28. The process according to claim 26, wherein each of said casing parts is manufactured by a first injection molding process with a first plastic material, and said bounding of each of said sealing frames to a corresponding casing part is effected by a second injection molding process with a second plastic material.

29. The process according to claim 26, wherein said second plastic material is softer than said first plastic material.

30. The process according to claim 27, wherein said welding process for bonding said inserted locking frame onto said casing part is an ultrasonic welding process.

31. A system for carrying out evaluation and/or monitoring methods involving electro-optical reading of an active surface of a chip shaped carrier, said system comprising
(a) a cartridge having a processing chamber and an opening for introducing a liquid sample into said processing chamber, said cartridge comprising a casing part,
(b) said casing part having an inner surface which faces said processing chamber and an outer surface, a first cavity for receiving a chip shaped carrier, and means which provide visual access to said first cavity and thereby to said active surface of said chip shaped carrier,
said first cavity having a bottom surface and inclined side wall surfaces which extend either between said inner surface or between said outer surface of said casing part and said bottom surface and which form an obtuse angle with that bottom surface,
(c) a sealing frame which is part of said casing part and which is made of a compressible material, said sealing frame being connected to said bottom surface of said first cavity,
(d) a locking frame,
(e) the shape and dimensions of said first cavity, said chip shaped carrier, said sealing frame, and said locking frame being such that
(e.1) said chip shaped carrier fits into the space delimited by said sealing frame, and a gap exists between said sealing frame and the inclined side wall surfaces of said first cavity,
(e.2) said locking frame is larger than said gap, said locking frame is however insertable into said gap by pressure exerted on said locking frame against said casing part, said pressure causing a compression of said sealing frame and a corresponding pressure on a substantial part of the outer surface of the lateral periphery of said chip shaped carrier, said outer surface of said chip shaped carrier being in contact with said sealing frame, and
(f) a chip shaped carrier having an active surface which is adapted to be read by an electro-optical reading device, said chip shaped carrier being positioned in said first cavity of said casing part.

32. A system according to claim 31, said system further comprising means for electro-optically reading said active surface of said chip shaped carrier.

* * * * *